United States Patent
Shirahata et al.

(10) Patent No.: US 8,818,060 B2
(45) Date of Patent: Aug. 26, 2014

(54) MEDICAL IMAGE DISPLAY DEVICE AND METHOD

(75) Inventors: Takashi Shirahata, Tokyo (JP); Hiroto Kokubun, Tokyo (JP); Yoshihiro Goto, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 374 days.

(21) Appl. No.: 13/142,014

(22) PCT Filed: Dec. 22, 2009

(86) PCT No.: PCT/JP2009/071289
§ 371 (c)(1),
(2), (4) Date: Jun. 24, 2011

(87) PCT Pub. No.: WO2010/074058
PCT Pub. Date: Jul. 1, 2010

(65) Prior Publication Data
US 2011/0255755 A1 Oct. 20, 2011

(30) Foreign Application Priority Data

Dec. 25, 2008 (JP) ................. 2008-329189

(51) Int. Cl.
| | |
|---|---|
| *G06K 9/00* | (2006.01) |
| *G06K 9/36* | (2006.01) |
| *G06K 9/32* | (2006.01) |
| *G06T 19/00* | (2011.01) |
| *G06T 15/40* | (2011.01) |
| *G09G 5/00* | (2006.01) |
| *G06F 19/00* | (2011.01) |
| *A61B 6/03* | (2006.01) |
| *A61B 5/055* | (2006.01) |

(52) U.S. Cl.
CPC .............. *G06T 19/00* (2013.01); *G06F 19/321* (2013.01); *A61B 6/03* (2013.01); *A61B 5/055* (2013.01)
USPC ........... 382/128; 382/131; 382/132; 382/284; 382/286; 382/295; 345/421; 345/581

(58) Field of Classification Search
USPC ......................................... 382/128, 130, 284
See application file for complete search history.

(56) References Cited

U.S. PATENT DOCUMENTS 6,928,314 B1 * 8/2005 Johnson et al. ............... 600/407
7,636,460 B2 * 12/2009 Verdonck ...................... 382/128
(Continued)

FOREIGN PATENT DOCUMENTS

| JP | 2004-522464 | 7/2004 |
| JP | 2004-529715 | 9/2004 |

(Continued)

OTHER PUBLICATIONS
International Search Report in PCT/JP2009/071289.

*Primary Examiner* — Matthew Bella
*Assistant Examiner* — Jose M Torres
(74) *Attorney, Agent, or Firm* — Cooper & Dunham LLP

(57) ABSTRACT

In a medical image display device for displaying a hollow organ of an examinee as a panoramic image, in order to inform an operator of the existence or nonexistence of a blind area in a panoramic image, the medical image display device has a panoramic image creating unit configured to create a panoramic image of a hollow organ of an examinee and a display unit configured to display the panoramic image, and further has a blind area detecting unit configured to detect a blind area in the panoramic image and an informing unit configured to inform an operator of the existence or nonexistence of the blind portion. Furthermore, a medical image display method of the present invention has a panoramic image creating step that creates a panoramic image of a hollow organ of an examinee and a display step that displays the panoramic image, and further has a blind area detecting step that detects a blind area in the panoramic image and an informing step that informs an operator of the existence or nonexistence of the blind portion.

14 Claims, 18 Drawing Sheets

(56) References Cited

U.S. PATENT DOCUMENTS

| | | | |
|---|---|---|---|
| 7,839,402 B2 * | 11/2010 | Dekel et al. | 345/421 |
| 8,514,218 B2 * | 8/2013 | Hong et al. | 345/419 |
| 2003/0007673 A1 | 1/2003 | Truyen et al. | |
| 2004/0264778 A1 * | 12/2004 | Liang et al. | 382/203 |
| 2006/0221074 A1 | 10/2006 | Matsumoto | |
| 2007/0003131 A1 | 1/2007 | Kaufman | |
| 2008/0069419 A1 * | 3/2008 | Farag et al. | 382/131 |

FOREIGN PATENT DOCUMENTS

| | | |
|---|---|---|
| JP | 2006-68301 | 3/2006 |
| JP | 2008-42235 | 2/2008 |

* cited by examiner

FIG.5
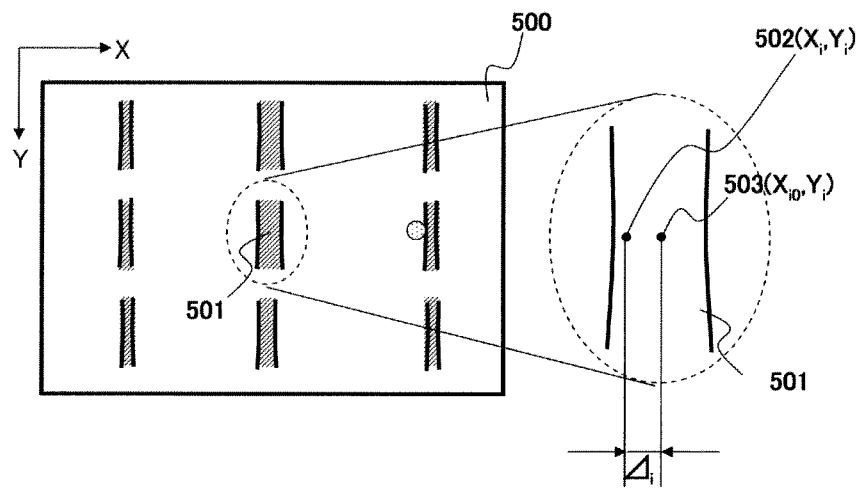
(a)
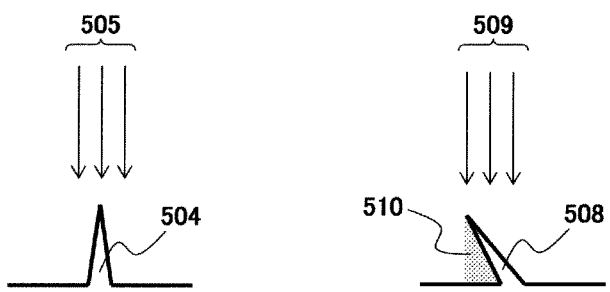
(b)
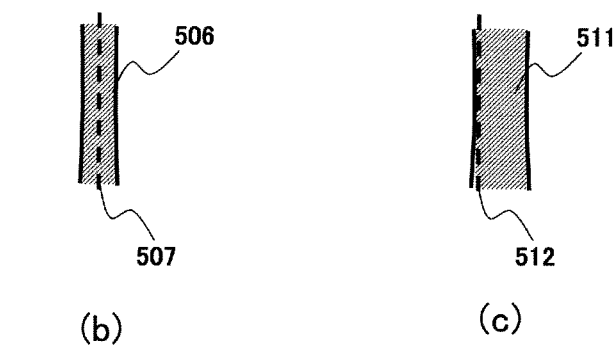
(c)

FIG.13
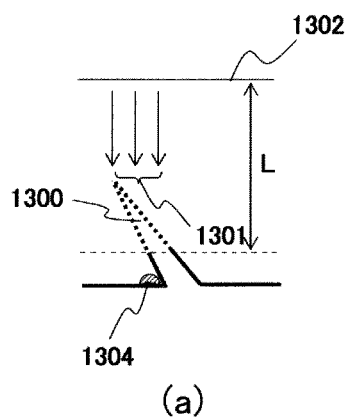
(a)
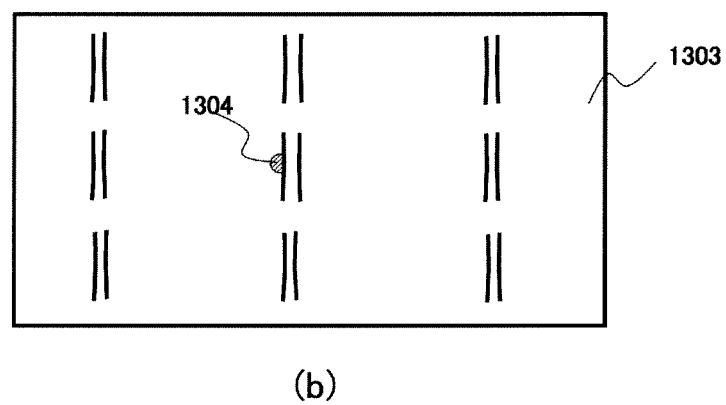
(b)

MEDICAL IMAGE DISPLAY DEVICE AND METHOD

TECHNICAL FIELD

The present invention relates to a medical image display device using a medical image obtained from a medical image diagnosing device such as an X-ray CT device, an MRI device, an ultrasonic device, and a method for the same, and relates to a technique of displaying the inside of a hollow organ being noted.

BACKGROUND ART

A method of calculating a line passing through a neighborhood of the center in a hollow organ (hereinafter referred to as "core line") and successively displaying virtual endoscope images along the core line (for example, patent document 1) is known as an image display method for enabling efficient diagnosis of the inside of a hollow organ such as a large bowel, bronchial tubes, blood vessels, etc. However, when a hollow organ having folds such as a large bowel or the like is observed, the back side of a fold becomes a blind area in the virtual endoscope display, and thus there is a probability that a lesion is overlooked.

An image obtained by slicing open a hollow organ in a longitudinal direction (hereinafter referred to as "panoramic image") is known as another image display method for observing a hollow organ. The panoramic image is obtained, for example, by setting each point on a core line (hereinafter referred to as "observing point") as a light source, radially radiating rays (virtual light beams) in a luminal wall direction within a cross-section on which a directional vector of the core line at an observing point position is set as a normal vector, thereby performing ray-casting, and performing rendering processing (for example, patent document 2). According to this method, as compared with a case where a virtual endoscope image is observed along a core line in a forward direction, a blind area caused by a structure such as a fold or the like can be reduced.

PRIOR ART DOCUMENT

Patent Document

Patent Document 1: Japanese Patent No. 3,632,862
Patent Document 2: Japanese Patent No. 3,627,066
Patent Document 3: JP-A-2006-42969

SUMMARY OF THE INVENTION

Problem to be Solved by the Invention

Even in the case of the panoramic image, when a structure such as a fold or the like exists obliquely to rays during rendering, an area which is located at the shadow of the structure becomes a blind area, and thus an operator may overlook a lesion when the lesion exists in the blind area. Therefore, the operator must observe in consideration of whether any blind area exists in a panoramic image or not. However, it is difficult to know the existence or nonexistence of a blind area by merely observing the panoramic image.

The present invention has been implemented in view of the foregoing circumstances, and has an object to enable an operator to be informed of the existence or nonexistence of a blind area in a panoramic image in a medical image display device for displaying a hollow organ of an examinee as a panoramic image.

Means of Solving the Problem

In order to attain the above object, according to the present invention, a medical image display device having a panoramic image creating unit configured to create a panoramic image of a hollow organ of an examinee and a display unit configured to display the panoramic image is characterized by including a blind area detecting unit configured to detect a blind area in the panoramic image and an informing unit configured to inform an operator of the existence or nonexistence of the blind portion.

Furthermore, according to the present invention, a medical image display method including a panoramic image crating step that creates a panoramic image of a hollow organ of an examinee and a display step that displays the panoramic image is characterized by including a blind area detecting step that detects a blind area in the panoramic image and an informing step that informs an operator of the existence or nonexistence of the blind portion.

Effect of the Invention

According to the present invention, the existence or non-existence of the blind area can be informed to the operator, and thus a lesion can be suppressed from being overlooked.

BRIEF DESCRIPTION OF THE DRAWINGS

FIG. 5 is a diagram for supplemental explanation of the first example of the flow of the processing of detecting a blind area.

FIG. 13 is a diagram showing a second example of the processing of creating a blind-area reduced image.

MODE FOR CARRYING OUT THE INVENTION

Figure 1:
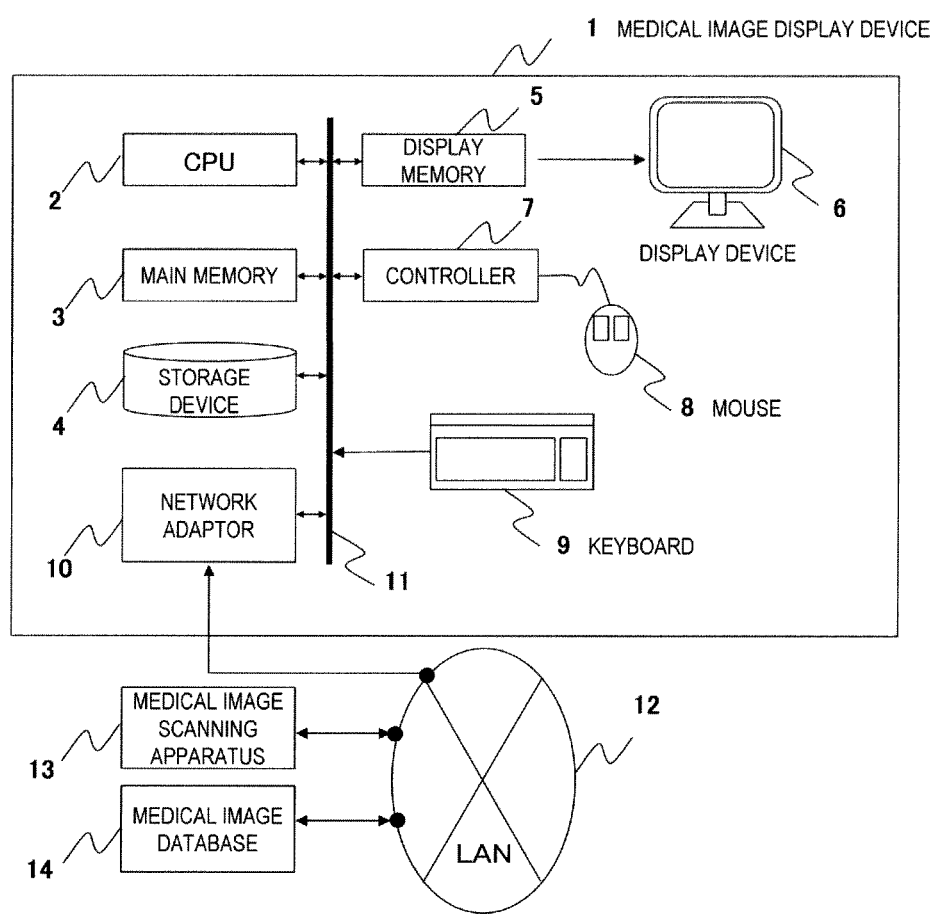
FIG. 1 is a diagram showing the hardware construction of a medical image display device according to the present invention.

A preferred embodiment of a medical image display device according to the present invention will be described hereunder with reference to the accompanying drawings. In the following description and accompanying drawings, the constituent elements having the same functions are represented by the same reference numerals, and the duplicative description thereof is omitted.

A preferred embodiment of a medical image display device according to the present invention will be described hereunder with reference to the accompanying drawings. In the following description and accompanying drawings, the constituent elements having the same functions are represented by the same reference numerals, and the duplicative description thereof is omitted.

FIG. 1 is a diagram showing the hardware construction of a medical image display device 1. The medical image display device 1 has CPU (Central Processing Unit) 2, a main memory 3, a storage device 4, a display memory 5, a display device 6, a controller 7 connected to a mouse 8, a keyboard 9, and a network adaptor 10 which are connected to one another through a system bus 11 so that signals can be transmitted and received among them. The medical image display device 1 is connected to a medical image scanning apparatus 13 and a medical image data base 14 through a network 12 so that signals can be received and transmitted. Here, "the signals can be received and transmitted" represents a state that a signal can be received/transmitted mutually or from one to another irrespective of electrical, optical, wired or wireless style.

CPU 2 is a device for controlling the operation of each constituent element. CPU 2 loads into the main memory 3 programs and data necessary for execution of the programs which are stored in the storage device 4, and execute the programs. The storage device 4 is a device for storing medical image information scanned by the medical image scanning apparatus 13, and specifically it is a hard disk or the like. Furthermore, the storage device 4 may be a device for receiving/transmitting data from/to a portable recording medium such as a flexible disk, an optical (magnetooptic) disk, a ZIP memory, an USB memory or the like. The medical image information is obtained from the medical image scanning apparatus 13 or the medical image data base 14 through the network 12 such as LAN (Local Area Network) or the like. In the storage device 4 are stored programs to be executed by CPU 2 and data necessary for executing the programs. The main memory 3 stores the programs to be executed by CPU 2 and processing results of the computing processing.

The display memory 5 temporarily stores display data to be displayed on the display device 6 such as a liquid crystal display, CRT (Cathode Ray Tube) or the like. The mouse 8 and the keyboard 9 are operating devices through which an operator makes an operation instruction to the medical image display device 1. The mouse 8 may be another pointing device such as a track pad, a trackball or the like. The controller 7 detects the state of the mouse 8, obtains the position of a mouse pointer on the display device 6 and outputs the obtained position information, etc. to CPU 2. The network adaptor 10 is used to connect the medical image display device 1 to the network 12 such as LAN, a telephone line, the Internet or the like.

The medical image scanning apparatus 13 is a device for obtaining medical image information such as a tomographic image or the like of an examinee. The medical image scanning apparatus 13 is an MRI device, an X-ray CT device, an ultrasonic diagnosing device, a scintillation camera device, a PET device, a SPECT device or the like. The medical image data base 14 is a data base system for storing medical image information scanned by the medical image scanning apparatus 13.

CPU 2 executes a method described later, whereby a panoramic image in which a hollow organ is cut open in a longitudinal direction is created and the created panoramic image is displayed on the display device 6. There is a risk that a blind area occurs in the panoramic image due to a structure such as a fold or the like existing on the inner wall of the hollow organ, and thus an operator must observe the panoramic image in consideration of the existence or nonexistence of a blind area in the panoramic image. However, it is difficult to know the existence or nonexistence of a blind area by merely observing the panoramic image.

Therefore, according to the present invention, it is determined whether a blind area exists or non-exists in a panoramic image, and the operator is informed of a determination result. Furthermore, according to the present invention, when some blind area exists in the panoramic image, a blind-area reduced image in which a blind area is displayed is created and displayed in the panoramic image or separately from the panoramic image.

First Embodiment

Figure 2:
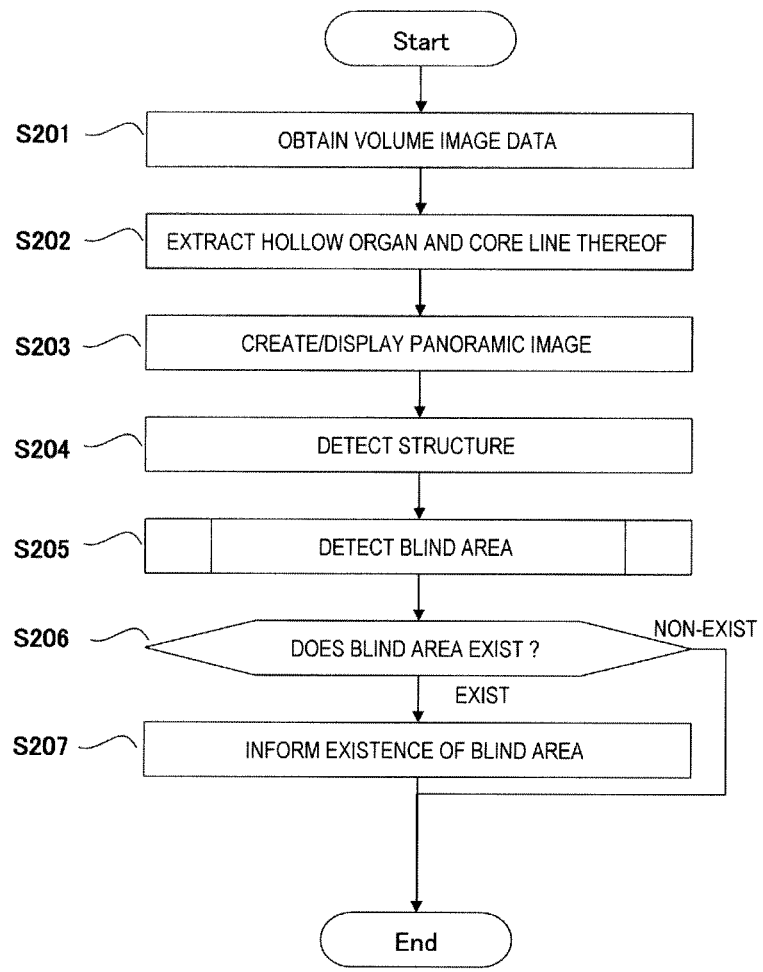
FIG. 2 is a diagram showing the flow of processing according to a first embodiment of the present invention.

FIG. 2 is a diagram showing the flow of processing according to an embodiment of determining the existence or nonexistence of a blind area in a panoramic image and informing a determination result to an operator. Each step of FIG. 2 will be described hereunder in detail.

(Step S201)

CPU 2 obtains volume image data of an examinee selected by operator's operation of the mouse 8 or the keyboard 9 from the medical image scanning apparatus 13 or the medical image data base 14 through the network 12. Here, the volume image data includes several tens to several hundreds of tomographic images obtained by scanning the examinee, and are constructed by sequentially arranging the tomographic images in some direction, for example, in a direction vertical to a cross-sectional plane.

(Step S202)

CPU 2 extracts a hollow organ as an observation target and a core line thereof from volume image data obtained in step S201. An extracting method based on threshold-value processing using upper and lower limit values of pixel values corresponding to the hollow organ as an extraction target, a publicly-known region growing method (Region Growing method), etc. are known as a method of extracting a hollow organ. A method described in Patent Document 3 is known as a method of extracting a core line, for example.

(Step S203)

Figure 3:
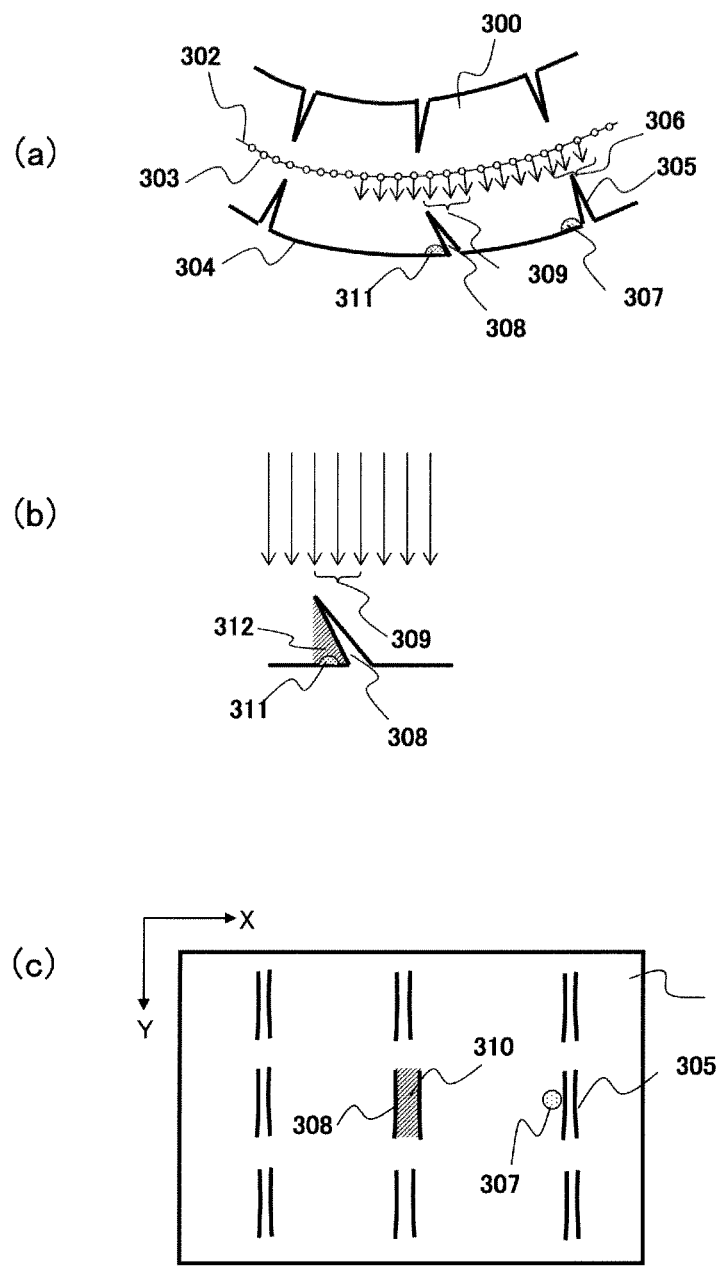
FIG. 3 is a diagram for supplemental explanation of a step S203 of the first embodiment.

CPU 2 creates a panoramic image on the basis of an extraction result of step S202, and displays the created panoramic image on the display device 6 through the display memory 5. The panoramic image may be created by using the method described in the Patent Document 2, for example. In this case, the method of creating the panoramic image will be briefly described with reference to FIG. 3. FIG. 3(a) is a cross-sectional view of a hollow organ 300 taken along a core line 302. CPU 2 sets plural observing points 303 on the core line 302, radially radiates rays (virtual light beams) in a direction to the wall of lumen from each observing point 303 within a cross-section perpendicular to the core line 302 at each observing point 303 to perform ray-casting, and performs rendering processing, thereby creating a panoramic image 301 as shown in FIG. 3(*c*). In the panoramic image 301 as shown in FIG. 3(*c*), a direction parallel to the core line 302 is set to an X-direction, and a peripheral direction of the inner wall of lumen 304 is set to a Y-direction. CPU 2 simultaneously obtains depth data representing the distance from each observing point 303 to the inner wall of lumen 304 or a fold existing on the inner wall in the process of the rendering processing.

In the process of the rendering processing, in a case where a fold exists substantially in parallel to rays 306 like a fold 305 shown in FIG. 3(*a*), even when a polyp 307 or the like exists in proximity to the fold 305, the polyp 307 is depicted on a panoramic image 301 shown in FIG. 3(*c*). On the other hand, when a fold exists obliquely to rays 309 like a fold 308 which is shown in FIG. 3(*b*) while scaled up, an area 312 becomes a blind area, and a polyp 311 or the like existing in proximity to the fold 308 are not depicted on the panoramic image 301, so that the operator may overlook the polyp 311 or the like.

(Step S204)

CPU 2 detects a structure in a lumen, for example, a fold in a large bowel on the basis of depth data obtained in step S203. Depth data Dplica from each observing point 303 to a fold 305 or fold 308 as a structure in the lumen is smaller than depth data Dwall from each observing point 303 to the inner wall of lumen 304. Therefore, an area whose depth data is smaller than α·Dwall obtained by multiplication of Dwall and a predetermined coefficient α which is not more than 1 is detected as a structure area. In FIG. 3(*c*), the structure area 310 detected on the periphery of the fold 308 is displayed in a hatching display style on the panoramic image 301.

In this step, the shape of the detected structure may be numerically converted as a shape index S by using expression (1), for example, and only a structure having a desired shape may be detected on the basis of the shape index S.

$$S = A\left[\frac{1}{2} - \frac{1}{\pi}\tan^{-1}\left(\frac{\lambda_1 + \lambda_2}{\lambda_1 - \lambda_2}\right)\right] \quad (1)$$

Here, A represents a normalization constant, and $\lambda_1$, $\lambda_2$ represents principal curvature at each point on the panoramic image. The shape index S represented by the expression (1) varies in accordance with whether the target structure is hemispherical (convex), semicylindrical (convex) or flat. Accordingly, only the semicylindrical (convex) structure can be detected through the threshold-value processing, for example. By detecting only a structure having a specific shape, the detection precision when a blind area is detected at the rear stage of this step can be enhanced.

(Step S205)

Figure 4:
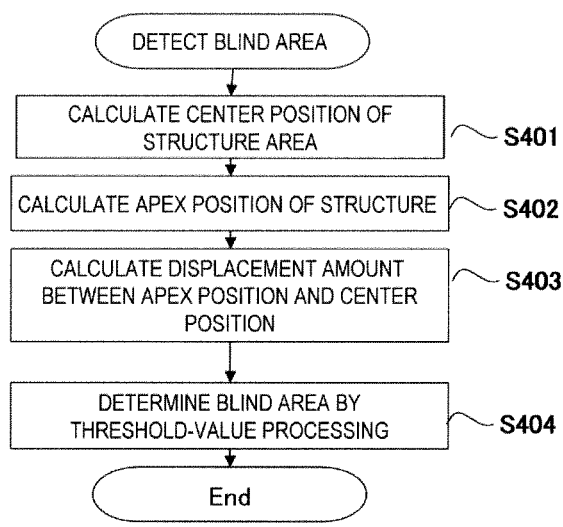
FIG. 4 is a diagram showing a first example of the flow of processing of detecting a blind area.

CPU 2 detects a blind area formed by the structure detected in step S204. FIG. 4 shows a first example of the flow of processing of detecting the blind area, and each step will be described below with reference to FIG. 5. In FIG. 5, the X-direction and the Y-direction with respect to panoramic image 500 are the same as those shown in FIG. 3 with respect to panoramic image 301.

(Step S401)

CPU 2 calculates the center position in the X-direction of a structure area for each structure (e.g. 501 in FIG. 5) detected in step S204. The center position in the X-direction may be calculated every Y-coordinate or an average value calculated in the Y-direction may be set as a representative value of each structure. In FIG. 5(*a*), the point of the center position $X_{i0}$ in the X-direction at the $Y_i$ coordinate is represented by 503.

(Step S402)

CPU 2 calculates an apex position in the X-direction of the structure on the basis of the depth data for each structure detected in step S204. The apex position in the X-direction may be calculated every Y-coordinate, or an average value calculated in the Y-direction may be set as a representative value of each structure. In FIG. 5(*a*), the point of the apex position $X_i$ in the X-direction at the $Y_i$ coordinate is represented by 502. This step may be executed prior to the step S401.

(Step S403)

CPU 2 calculates the displacement amount between the center position of the structure area calculated in step S401 and the apex position of the structure calculated in step S402. In FIG. 5(*a*), the displacement amount between the point 503 of the center position $X_{i0}$ and the point 502 of the apex position $X_i$ is represented as $\Delta_i = |X_{i0} - X_i|$. When the center position and the apex position are calculated every Y coordinate in step S401 and step S402, the average value $\Delta_{ave}$ of the displacement amount may be calculated by using the expression (2).

$$\Delta ave = \frac{1}{N}\sum_{i=1}^{N}\Delta i \quad (2)$$

Here, N represents the number of samples in the Y-direction to calculate the displacement amount, and the sampling interval may be set to one or more pixels.

(Step S404)

CPU 2 compares the displacement amount $\Delta_i$ calculated in step S403 with a predetermined threshold value. In the case of a fold 504 which exists substantially in parallel to a ray 505 as shown in FIG. 5(*b*) and thus does not form a blind area, the apex position 407 of the structure is substantially equal to the center position of the structure area 406, and thus the displacement amount decreases. On the other hand, in the case of a fold 508 which exists obliquely to a ray 509 as shown in FIG. 5(*c*) and thus forms a blind area 510, the displacement amount between the apex position 512 of the structure and the center position of the structure area 511 increases. Accordingly, the blind area can be detected by the threshold-value processing. A conditional expression of expression (3) may be used for the threshold value processing.

$$\frac{\Delta ave}{L} > T \quad (3)$$

Here, L represents the average distance in the X-direction of the structure, and T represents a predetermined threshold value.

According to the flow of the processing described above, the blind area in the panoramic image can be detected.

Figure 6:
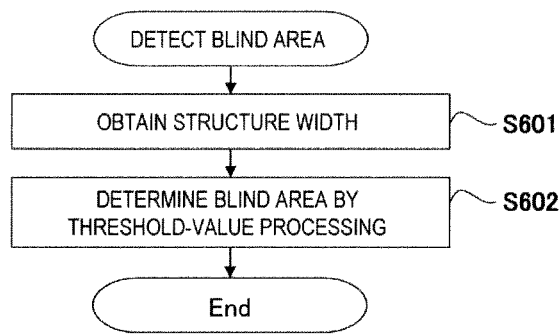
FIG. 6 is a diagram showing a second example of the flow of the processing of detecting the blind area.
Figure 7:
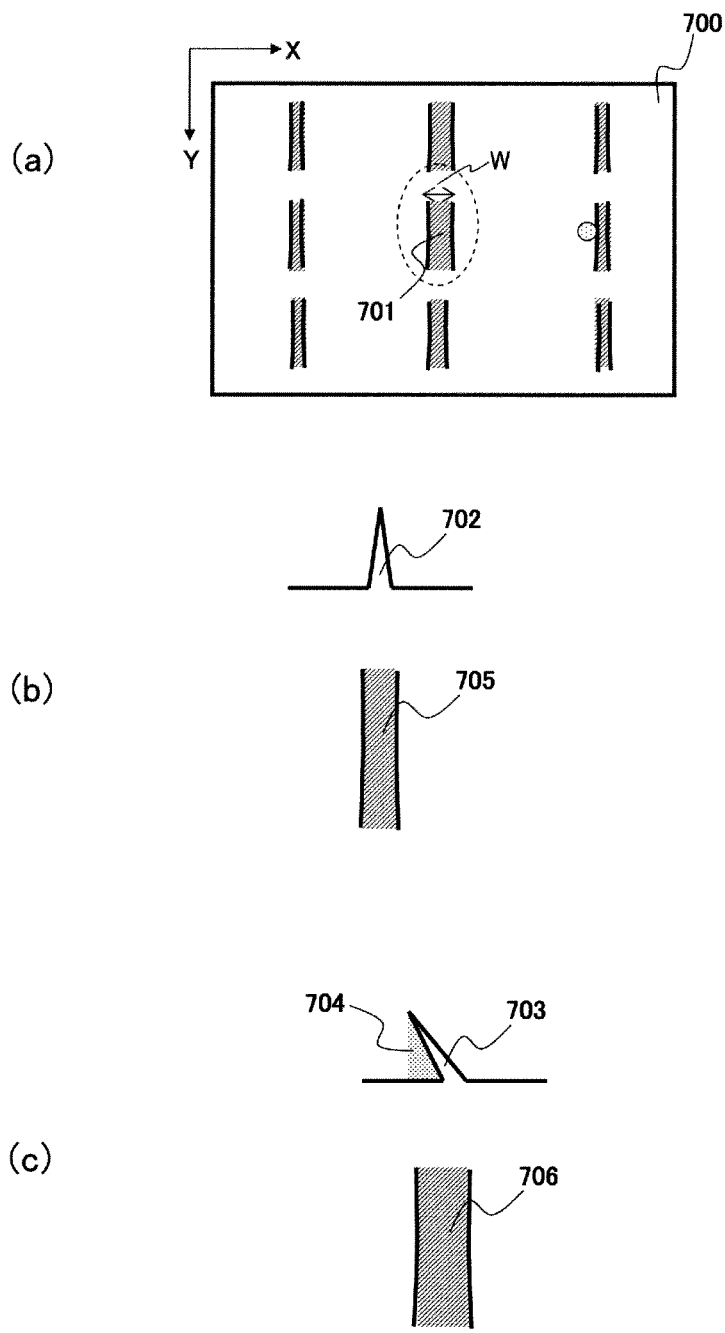
FIG. 7 is a diagram for supplemental explanation of the second example of the flow of the processing of detecting the blind area.

Next, FIG. 6 shows a second example of the flow of the processing of detecting a blind area, and each step will be described hereunder with reference to FIG. 7.

(Step S601)

CPU 2 calculates the width of the structure area for each structure detected in step S204. FIG. 7(a) shows the width W of a structure area with respect to a fold 701. The width W may be set to the average value in the Y direction for each structure, or a mode value may be used.
(Step S602)
CPU 2 compares the width W of the structure area calculated in step S601 with a predetermined threshold value. In the case of a fold 702 which does not form any blind area as shown in FIG. 7(b), the width W of the structure area 705 decreases, however, in the case of a fold 703 which forms a blind area 704 as shown in FIG. 7(c), the width W of the structure area 706 increases. Accordingly, the blind area can be detected by the threshold-value processing.

According to the second example of the processing of detecting the blind area, the number of steps is smaller than the first example, and thus the processing speed can be increased.

Figure 8:
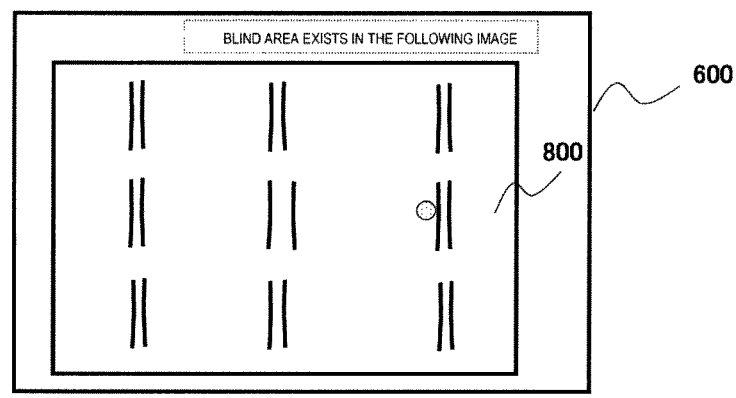
FIG. 8 is a diagram showing an example in which existence of a blind area is informed.

The example of the processing of detecting the blind area is not limited to these examples, and a combination of the first example and the second example may be used. For example, detection of a blind area may be determined when both the conditions of the first and second examples are satisfied, or detection of a blind area may be determined when any one condition is satisfied.
(Step S206)
CPU 2 determines on the basis of the detection result of step S205 whether a blind area exists in the panoramic image. The processing goes to step S207 when a blind area exists, or goes to finishing when no blind area exits.
(Step S207)
CPU 2 informs the operator of existence of the blind area. The informing method may be based on screen display on the display device 6 or based on a voice message. FIG. 8 shows an example of the screen display. In the example shown in FIG. 8, not only a panoramic image 800, but also character information representing that a blind area exists in the panoramic image are displayed. By the screen display described above, the operator can know the existence of the blind area.

Figure 9:
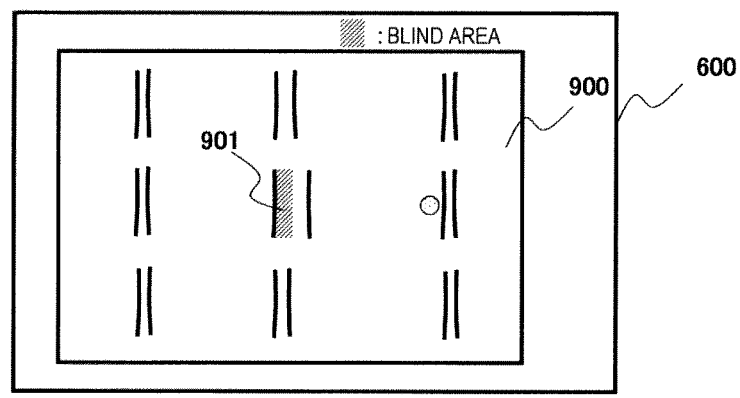
FIG. 9 is a diagram showing another example in which existence of a blind area is informed.

Furthermore, FIG. 9 shows another example of the screen display. In an example of FIG. 9, the position of a blind area existing in the panoramic image 900 displayed on a screen 600 is indicated while colored with a marker 901. By the screen display described above, the operator can know not only the existence of the blind area, but also the position of the blind area.

Second Embodiment

Figure 10:
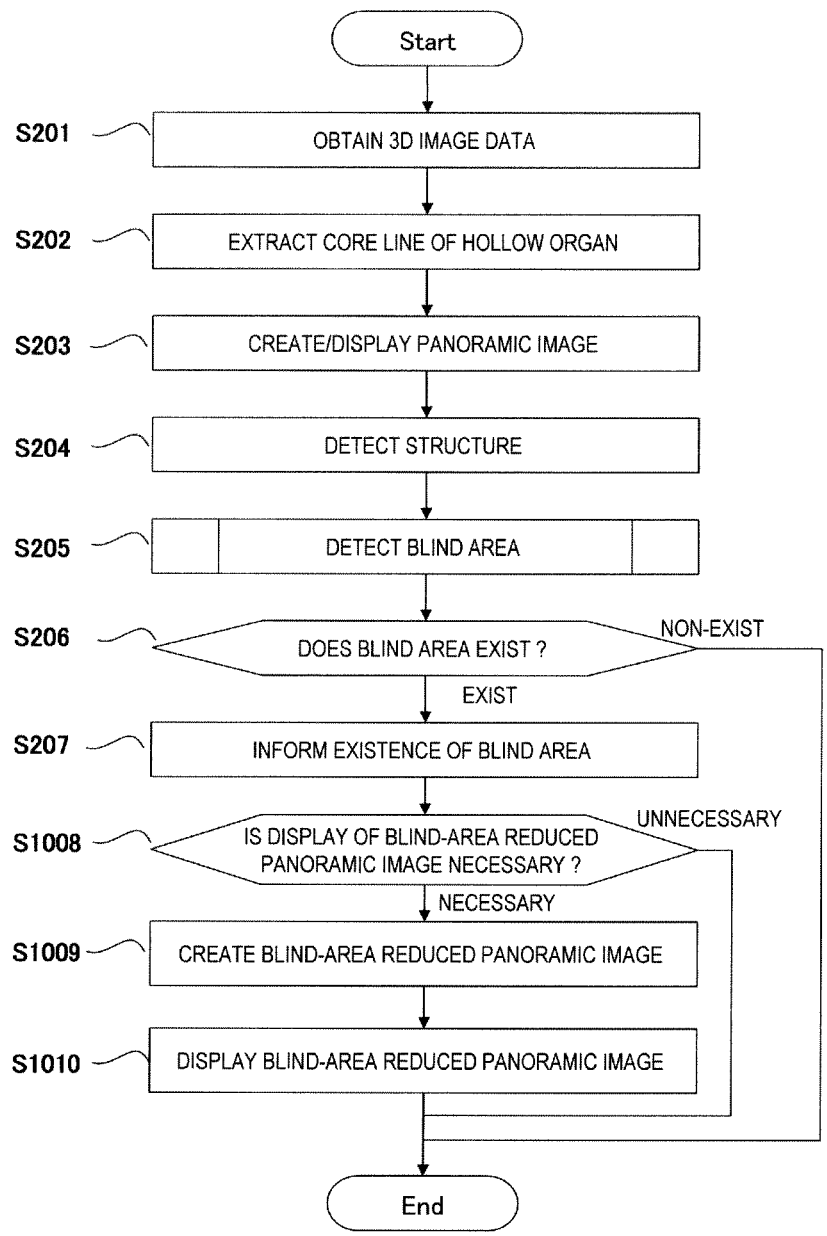
FIG. 10 is a diagram showing the flow of processing according to a second embodiment of the present invention.
Figure 11:
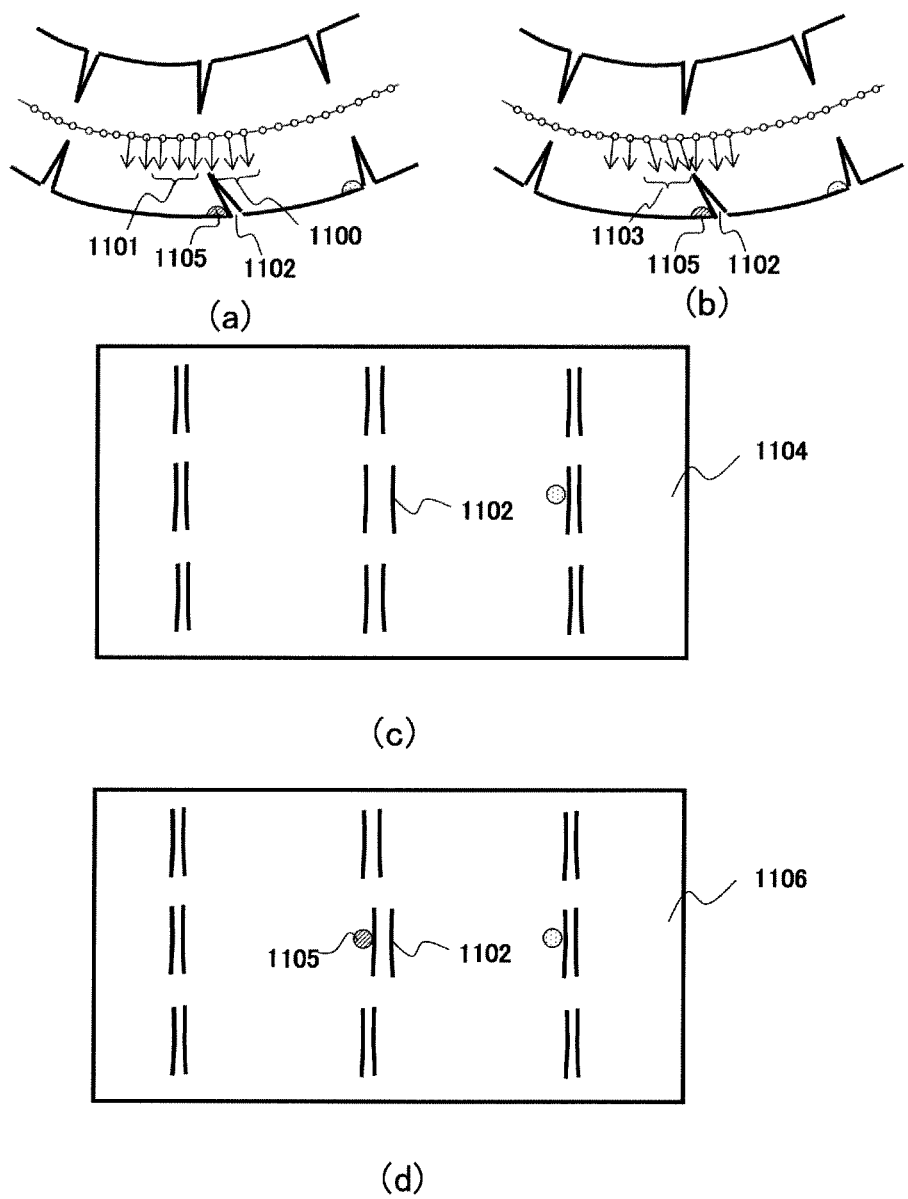
FIG. 11 is a diagram showing a first example of the processing of creating a blind-area reduced image.

FIG. 10 is a diagram showing the flow of processing according to this embodiment in which the existence or nonexistence of a blind area in a panoramic image is determined, a determination result is informed to the operator, a blind-area reduced image representing an aspect of a blind area is created when the blind area exists in the panoramic image, and the blind-area reduced image is displayed in the panoramic image or separately from the panoramic image. Each step of FIG. 10 will be described hereunder in detail. The same steps as the first embodiment are represented by the same step numbers and the description thereof is omitted.
(Steps S201 to S207)
The steps are the same as the first embodiment.
(Step S1008)
CPU 2 determines whether it is necessary to display a blind-area reduced image created by reducing the blind area. When the determination result indicates necessity, the processing goes to step S1009. When it is unnecessary, the processing is finished. As a determination method of this step, for example, when the displacement amount calculated in step S403 or the width calculated in step S601 is smaller than a predetermined threshold value, unnecessity is determined, and in the other cases, necessity is determined. Furthermore, it may be inquired to the operator whether it is necessary to display a blind-area reduced image, and necessity or unnecessity may be determined on the basis of an operator's input to the inquiry.
(Step S1009)
CPU 2 creates a blind-area reduced image. An example of creating the blind-area reduced image will be described hereunder.
(Creating Example 1 of Blind-Area Reduced Image)
An example 1 of creating a blind-area reduced image will be described with reference to FIG. 11. FIG. 11(a) is a diagram showing the directions of rays when a normal panoramic image is created. A fold 1102 exists obliquely to the rays. Therefore, a created panoramic image as shown in FIG. 11(c) is obtained, and a polyp 1105 located at a blind area portion of the fold 1102 is not displayed in a panoramic image 1104. Therefore, in this creating example, the directions of some rays are changed so that the polyp 1105 located in the blind area is displayed in the panoramic image. FIG. 11(b) is a diagram showing an aspect that the directions of some rays are changed. The direction of some rays 1101 in FIG. 11(a) is changed to a direction which is substantially parallel to the fold 1102 as in the case of rays 1103 in FIG. 11(b), whereby a blind-area reduced image 1106 in which the polyp 1105 is displayed as shown in FIG. 11(d) can be created.

Figure 12:
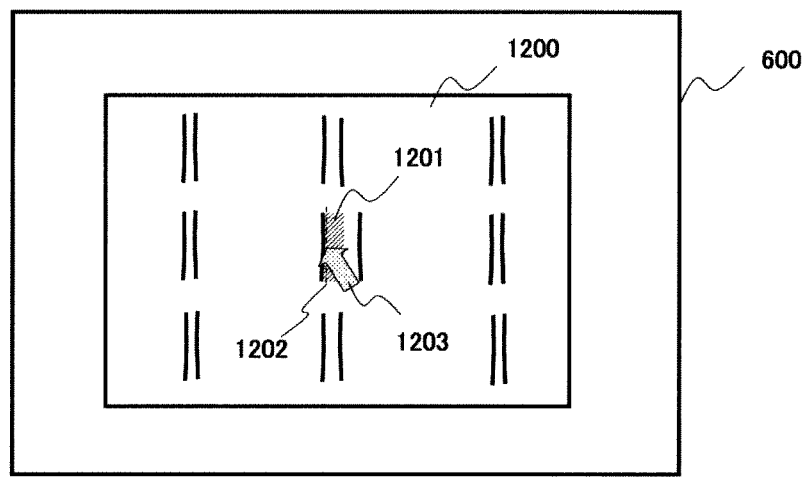
FIG. 12 is a diagram for supplemental explanation of the first example of the processing of creating the blind-area reduced image.

The ray changing angle may be set on the basis of the displacement amount determined in step S403 and the depth data of the inner wall of the lumen and the apex of the structure. Alternatively, the ray changing angle may be set on the basis of the amount of a drag operation which is performed on GUI (Graphical User Interface) as shown in FIG. 12 through the pointing device such as the mouse 8 or the like by the operator. In GUI of FIG. 12, a blind area 1201 displayed with being colored, an apex position marker 1202 representing the position of the apex of the structure and the pointer 1203 of the pointing device are displayed in the panoramic image 1200 displayed on the screen 600. The operator drag-operates the apex position marker 1202 by using the pointer 1203 of the pointing device while referring to the colored and displayed blind area 1201. CPU 2 changes the angle of the rays in accordance with the drag-operation amount, and updates the panoramic image of the blind area as a blind-area reduced image.

The rays whose directions are changed may be rays radiated to the structure area detected in step S204 and the periphery thereof, or rays which can be radiated over the width of the blind area. When the directions of the rays radiated to the structure area and the periphery thereof are changed, an image which makes it easy to know the positional relationship between the polyp existing in the blind area and the structure is obtained. When the directions of the rays which can be radiated over the width of the blind area are changed, a distortion area occurring in the panoramic image can be reduced.
(Creating Example 2 of Blind-Area Reduced Image)
An example 2 of creating a blind-area reduced image will be described with reference to FIG. 13. In this creating example, the transparence of a part of a structure forming a blind area is changed to create a panoramic image. For example, as shown in FIG. 13(a), when a panoramic image is created while the transparence of an area spaced from the core line 1302 of a hollow organ at a distance L is set to 100%, a panoramic image as shown in FIG. 13(b) is obtained. That is, by setting the transparence of the area of the distance L from the core line 1302 to 100%, a part 1300 of a fold as a structure forming a blind area does not substantially exist, and thus the rays 1301 can reach the polyp 1304. As a result, the polyp 1304 existing behind the part 1300 of the fold is displayed on the panoramic image, and a blind-area reduced image 1303 as shown in FIG. 13(*b*) is created. The transparence is not limited to 100%, and it may be set to such a transparence level that the operator can check the polyp 1304 existing behind the part 1300 of the fold.

A value which is empirically predetermined may be used as the value of the distance L from the core line 1302. Alternatively, it may be set on the basis of the depth data in proximity to the blind area or the displacement amount determined in step S403. Alternatively, CPU 2 may change the distance L and update the panoramic image of the blind area as the blind-area reduced image every time the operator inputs on GUI which can input the distance L interactively.

The transparence-changed area is not limited to the blind area, and the transparence of the whole area within the distance L from the core line 1302 of the hollow organ may be changed.

(Step S1010)

CPU 2 displays the blind-area reduced image created in step S1009 on the display device 6 through the display memory 5. Display examples will be described hereunder.

(Display Example 1 of Blind-Area Reduced Image)

Figure 14:
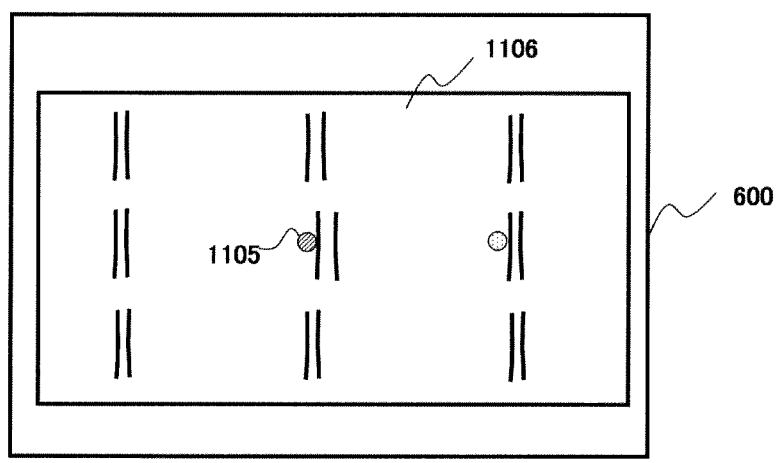
FIG. 14 is a diagram showing a first display example of a blind-area reduced image.

FIG. 14 shows this display example. In this display example, a blind-area reduced image 1106 created in step S1009 is displayed on the screen 600 of the display device 6. The image displayed on the screen 600 is not limited to the blind-area reduced image 1106, and it may be a blind-area reduced image 1303 created by changing the transparence of the part 1300 of the fold, or another blind-area reduced image.

By displaying the blind-area reduced image, the operator can easily observe the polyp 1105, etc. which are hidden in the blind area in the normal panoramic image, and thus a lesion can be suppressed from being overlooked.

(Display Example 2 of Blind-Area Reduced Image)

Figure 15:
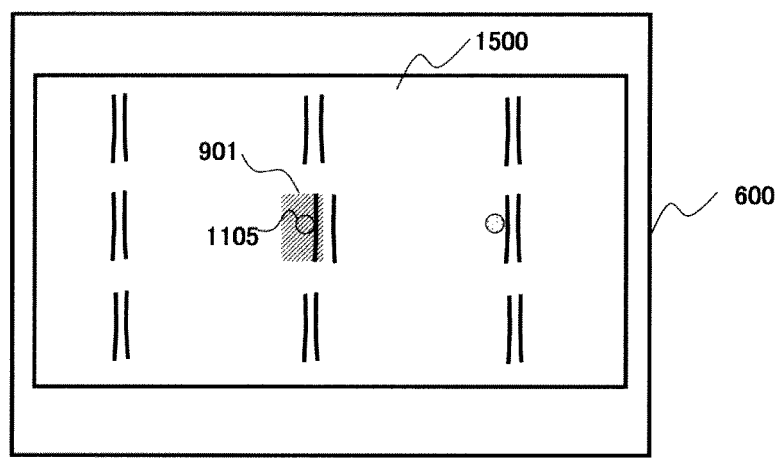
FIG. 15 is a diagram showing a second display example of a blind-area reduced image.

FIG. 15 shows this display example. In this display example, an image 1500 in which a marker 901 coloring the position of a blind area as shown in FIG. 9 is superimposed on the blind-area reduced image 1106 created in step S1009 is displayed on the screen 600 of the display device 6. In this display example, the blind-area reduced image is not limited to the blind-area reduced image 506.

By this display example, the operator can observe the blind-area reduced image while referring to the position of the blind area.

(Display Example 3 of Blind-Area Reduced Image)

Figure 16:
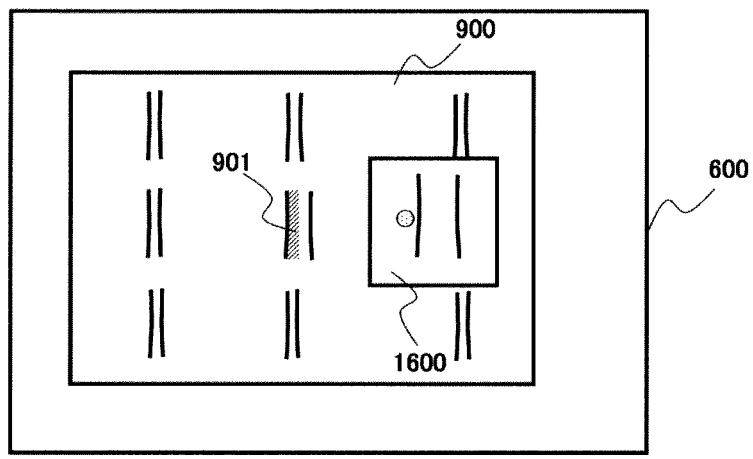
FIG. 16 is a diagram showing a third display example of a blind-area reduced image.

FIG. 16 shows this display example. In this display example, an image in which a blind-area reduced image 1600 created by reducing a blind area for only the peripheral portion of the blind area is superimposed on an image displayed while the position of the blind area existing in the panoramic image 900 is colored by the marker 901 is displayed on the screen 600 of the display device 6.

By this display example, the operator can observe a blind-area reduced image 1600 and a panoramic image 900 in which the blind area is not reduced while comparing the blind-area reduced image 1600 and the panoramic image 900.

(Display Example 4 of Blind-Area Reduced Image)

Figure 17:
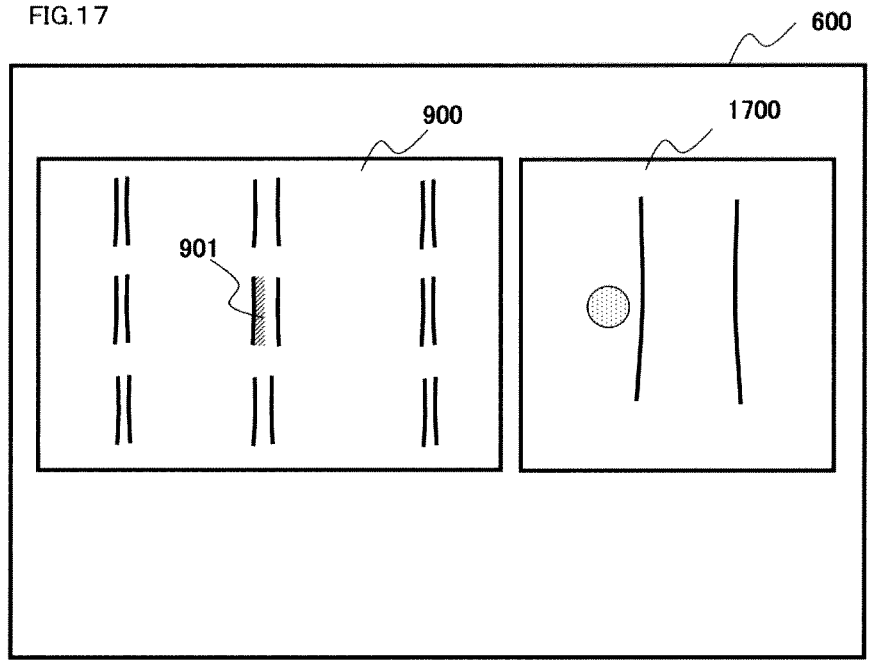
FIG. 17 is a diagram showing a fourth display example of a blind-area reduced image.

FIG. 17 shows this display example. In this display example, an image in which an image displayed by coloring the position of a blind area existing in the panoramic image by the marker 901 and a blind-area reduced image 1700 obtained by enlarging the blind-area reduced image 1600 in which the blind area is reduced for only the peripheral portion of the blind area are arranged side by side is displayed on the screen 600 of the display device 6.

By this display example, the operator can observe the blind-area reduced image 1700 and the whole panoramic image 900 in which the blind area is not reduced while comparing the blind-area reduced image 1700 and the whole panoramic image 900, and also can easily observe the details of the blind-area reduced image 1700.

(Display Example 5 of Blind-Area Reduced Image)

Figure 18:
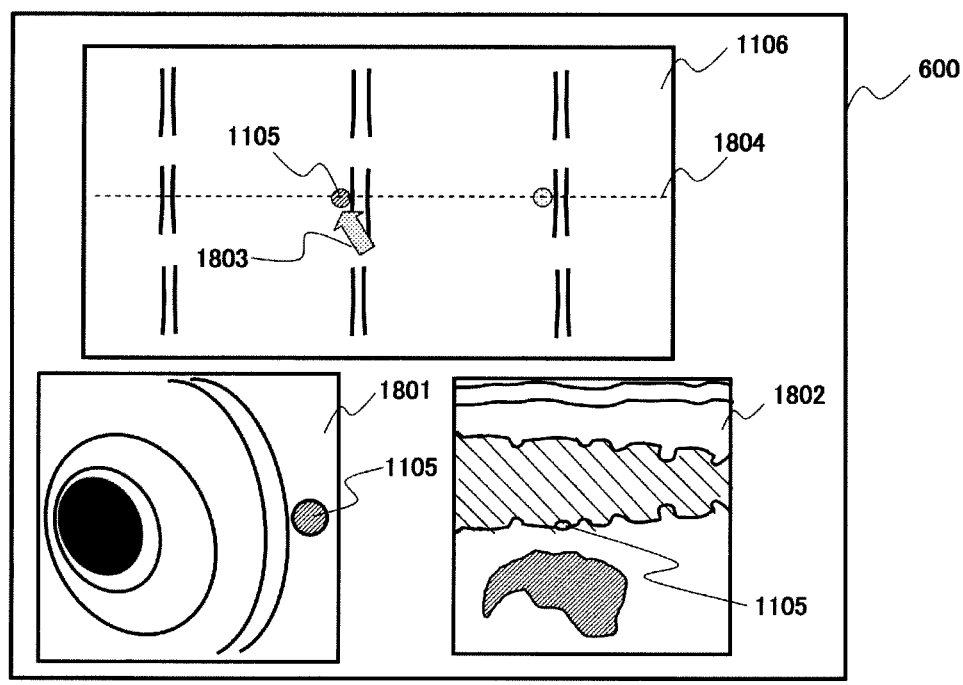
FIG. 18 is a diagram showing a fifth display example of a blind-area reduced image.

FIG. 18 shows this display example. In this display example, an image in which the blind-area reduced image 1106 created in step S1009, the virtual endoscope image 1801 containing the displayed polyp 1105 existing in the blind area and the MPR image 1802 are arranged side by side is displayed on the screen 600 of the display device 6. The virtual endoscope image 1801 and the MPR image 1802 may be simultaneously displayed, or may be selectively displayed on the basis of an operator's input. Furthermore, the operator may set an area of interest such as a line 1804 or the like through the mouse 8 or the keyboard 9 by operating the pointer 1803 on the blind-area reduced image 1106 so that the creation positions of the virtual endoscope image 1801 and the MPR image 1802, etc. are arbitrarily determined.

By this display example, the operator can observe not only the blind-area reduced image 1100, but also the virtual endoscope image 1801 and the MPR image 1802, and thus can perform multifaceted diagnosis.

According to the present invention described above, it is informed to the operator whether a blind area exists in a panoramic image or not. Furthermore, when a blind area exists in a panoramic image, a blind-area reduced image in which a blind area is displayed is created and displayed in the panoramic image or separately from the panoramic image. As a result, a diagnosis which is efficient and has less overlooking can be implemented under a lesion diagnosis of the inside of a lumen.

DESCRIPTION OF REFERENCE NUMERALS

1 medical image display device, 2 CPU, 3 main memory, 4 storage device, 5 display memory, 6 display device, 7 controller, 8 mouse, 9 keyboard, 10 network adaptor, 11 system bus, 12 network, 13 medical image scanning apparatus, 14 medical image data base

The invention claimed is:

1. A medical image display device comprising:
   a panoramic image creating unit configured to create a panoramic image of a hollow organ of an examinee;
   a display unit configured to display the panoramic image;
   a blind area detecting unit configured to detect a blind area which is located at a shadow of a structure existing on an inner wall of the hollow organ in the panoramic image; and
   an informing unit configured to inform an operator of the existence or nonexistence of the blind area,
   wherein the blind area detecting unit detects the blind area by comparing a first threshold value with a displacement amount between a center position of the structure in a core line direction of the hollow organ and an apex position of the structure in the core line direction or by comparing a second threshold value with a width of the structure in the core line direction.

2. The medical image display device according to claim 1, wherein the blind area detecting unit detects the blind area on the basis of the center position and the apex position of the structure existing on the inner wall of the hollow organ.

3. The medical image display device according to claim 1, wherein the blind area detecting unit detects the blind area on the basis of a width of the structure existing on the inner wall of the hollow organ.

4. The medical image display device according to claim 1, further comprising a blind-area reduced image creating unit configured to create a blind-area reduced image in which the blind area is reduced.

5. The medical image display device according to claim 4, wherein the blind-area reduced image creating unit changes a visual line direction in accordance with the blind area and creates a blind-area reduced image.

6. The medical image display device according to claim 4, wherein the blind-area reduced image creating unit changes transparence of at least a part of the structure and creates a blind-area reduced image.

7. A medical image display method comprising
a panoramic image creating step that creates a panoramic image of a hollow organ of an examinee;
a display step that displays the panoramic image;
a blind area detecting step that detects a blind area which is located at a shadow of a structure existing on an inner wall of the hollow organ in the panoramic image; and
an informing step that informs an operator of the existence or nonexistence of the blind area,
wherein the blind area detecting step detects the blind area by comparing a first threshold value with a displacement amount between a center position of the structure in a core line direction of the hollow organ and an apex position of the structure in the core line direction or by comparing a second threshold value with a width of the structure in the core line direction.

8. The medical image display method according to claim 7, wherein the blind area detecting step detects the blind area on the basis of the center position and the apex position of the structure existing on the inner wall of the hollow organ.

9. The medical image display method according to claim 7, wherein the blind area detecting step detects the blind area on the basis of a width of the structure existing on the inner wall of the hollow organ.

10. The medical image display method according to claim 7, further comprising a blind-area reduced image creating step to create a blind-area reduced image in which the blind area is reduced.

11. The medical image display method according to claim 10, wherein the blind-area reduced image creating step changes a visual line direction in accordance with the blind area and creates a blind-area reduced image.

12. The medical image display method according to claim 10, wherein the blind-area reduced image creating step changes transparency of at least a part of the structure and creates a blind-area reduced image.

13. A medical image display device comprising:
a panoramic image creating unit configured to create a panoramic image of a hollow organ of an examinee, by use of virtual light rays;
a display unit configured to display the panoramic image;
a blind area detecting unit configured to detect a blind area which is located at a shadow of a structure existing on an inner wall of the hollow organ in the panoramic image; and
a blind-area reduced image creating unit configured to create a blind-area reduced image in which the blind area is reduced by changing a direction of view line of some of the virtual light rays to be parallel with the structure but not changing a direction of view line of the other virtual light rays.

14. A medical image display device comprising:
a panoramic image creating unit configured to create a panoramic image of a hollow organ of an examinee;
a display unit configured to display the panoramic image;
a blind area detecting unit configured to detect a blind area which is located at a shadow of a structure existing on an inner wall of the hollow organ in the panoramic image; and
a blind-area reduced image creating unit configured to create a blind-area reduced image in which the blind area is reduced by setting transparency of a part of the structure forming the blind area to 100% transparency, wherein the part of the structure is located within a predetermined distance from a core line of the hollow organ.

* * * * *